United States Patent
Lee et al.

(10) Patent No.: US 10,697,027 B2
(45) Date of Patent: Jun. 30, 2020

(54) BIOLOGICAL DETECTION METHOD FOR DIOXINS IN SERUM, AND DIAGNOSTIC USE THEREFOR IN METABOLIC SYNDROME AND RELATED CONDITIONS

(71) Applicant: UNIVERSITY-INDUSTRY COOPERATION GROUP OF KYUNG HEE, Gyeonggi-do (KR)

(72) Inventors: Hong Kyu Lee, Yongsan-gu (KR); Youngmi Kim, Gangnam-gu (KR)

(73) Assignees: UNIVERSITY-INDUSTRY COOPERATION GROUP OF KYUNG HEE UNIVERSITY, Gyeonggi-do (KR); Hong Kyu Lee, Seoul (KR)

( * ) Notice: Subject to any disclaimer, the term of this patent is extended or adjusted under 35 U.S.C. 154(b) by 0 days.

(21) Appl. No.: 16/417,523

(22) Filed: May 20, 2019

(65) Prior Publication Data

US 2019/0309376 A1  Oct. 10, 2019

Related U.S. Application Data

(62) Division of application No. 15/051,385, filed on Feb. 23, 2016, now abandoned, which is a division of application No. 13/821,779, filed as application No. PCT/KR2011/006583 on Sep. 6, 2011, now abandoned.

(30) Foreign Application Priority Data

Sep. 10, 2010 (KR) .................. 10-2010-0088905

(51) Int. Cl.
*C12Q 1/6897* (2018.01)
*C12Q 1/66* (2006.01)
*G01N 33/53* (2006.01)

(52) U.S. Cl.
CPC .............. *C12Q 1/6897* (2013.01); *C12Q 1/66* (2013.01); *G01N 33/5308* (2013.01); *G01N 2800/04* (2013.01)

(58) Field of Classification Search
None
See application file for complete search history.

(56) References Cited

U.S. PATENT DOCUMENTS 5,854,010 A   12/1998   Denison et al.

FOREIGN PATENT DOCUMENTS

KR   20010046920 A   6/2001
KR   10-1272315      6/2013

OTHER PUBLICATIONS

Brunner et al. "Serum-free Cell Culture: The Serum-free Media Interactive Online Database" Altex (2010) vol. 27, pp. 53-62.
Sun et al. "Comparative analysis of dioxin response elements in human, mouse and rat genomic sequences" Nucleic Acids Research (2004) vol. 32, No. 15, pp. 4512-4523.
Meszaros et al. "Immunireactivity and bioactivity of lipopolysaccharide-binding protein in normal and heat-inactivated sera." Infection and Immunity (1995) vol. 63, No. 1, pp. 363-365.
Henriksen et al. "Serum Dioxin and Diabetes Mellitus in Veterans of Operation Ranch Hand" Epidemiology (1997) vol. 8, No. 3, pp. 252-258.
Murk et al. "The CALUX (Chemical-activated luciferase expression) assay adapted and validated for measuring TCDD equivalents in blood plasma", Environmental Toxicology and Chemistry (1997) vol. 16, No. 8, pp. 1583-1589.
Vondracek et al. "Monitoring river sediments contaminated predominantly with polyaromatic hydrocarbons by chemical and in vitro bioassay techniques," Environmental Toxicology and Chemistry (2001) vol. 20, No. 7, pp. 1489-1506.
Kasai et al. "Fast-track DRESSA: a bioassay for fast, sensitive, and selective detection of halogenated and polycyclic aromatic hydrocarbons," Analytical Biochemistry (2005) vol. 337, No. 1, pp. 84-88.
Lee et al. "A Strong Dose-Response Relation Between Serum Concentrations of Persistent Organic Pollutants and Diabetes: Results from the National Health and Examination Survey 1999-2002," Diabetes Care (2006) vol. 29, No. 7, pp. 1638-1644.

*Primary Examiner* — Channing S Mahatan
(74) *Attorney, Agent, or Firm* — Lando & Anastasi, LLP

(57) ABSTRACT

A biological detection method for dioxin compounds in serum and its diagnostic use in predicting metabolic syndrome and related conditions are disclosed. The method of detecting dioxin compounds include obtaining a serum sample by heat-inactivating total serum obtained from a subject, preparing a transformed cell line by introducing a recombinant vector comprising a gene construct in which at least one dioxin-responsive element is operably linked to a promoter and a reporter gene into a host cell, culturing the transformed cell line with the serum sample, detecting the activation of the reporter gene in the transformed cell line, and determining that the dioxin compound is included in the serum sample when the activation of the reporter gene is detected. The serum detected by the method can be used as a surrogate serum biomarker to correlate serum content with disease factors and to predict the occurrence of disease and determine treatability.

5 Claims, 11 Drawing Sheets

Specification includes a Sequence Listing.

SEQUENCE LISTING

```
<160> NUMBER OF SEQ ID NOS: 1

<210> SEQ ID NO 1
<211> LENGTH: 7
<212> TYPE: DNA
<213> ORGANISM: Mus musculus
<220> FEATURE:
<221> NAME/KEY: misc_feature
<222> LOCATION: (2)..(2)
<223> OTHER INFORMATION: n is a, c, g, or t

<400> SEQUENCE: 1 tngcgtg                                                                7
```

BIOLOGICAL DETECTION METHOD FOR DIOXINS IN SERUM, AND DIAGNOSTIC USE THEREFOR IN METABOLIC SYNDROME AND RELATED CONDITIONS

CROSS-REFERENCE TO RELATED APPLICATIONS

This application is a divisional of U.S. patent application Ser. No. 15/051,385, filed Feb. 23, 2016, which is a divisional of U.S. patent application Ser. No. 13/821,779, filed on Mar. 8, 2013, which is a national stage application under 35 U.S.C. § 371 of International Patent Application No. PCT/KR2011/006583, filed on Sep. 6, 2011, which claims priority to Korean Patent Application No. 10-2010-0088905, filed on Sep. 10, 2010. Each of these applications is incorporated herein by reference in its entirety for all purposes.

BACKGROUND

1. Field of Technology

The present invention relates to a novel biological detection method for dioxin like activity in serum and a diagnostic use thereof in metabolic syndrome and related conditions.

2. Description of the Related Art

Persistent organic pollutants (pops) do not exist in the nature or only very small amounts of them if they exist. They are mostly organic chemicals generated artificially for human needs or byproducts of industrialization. Dioxin and dioxin like substances are the representatives. Once POPs are come into human body, they are not easily decomposed or excreted, resulting in the accumulation in human body.

Recently, the public is more interested in the situation of these chemicals in our environment, including industrial byproducts, pesticides, or drugs cause potential endocrine disruption in human and many other wild species. Accordingly, many reports have been made saying that blood levels of various POPs such as dioxins, polychlorinated biphenyls, and organic phosphorous pesticides are closely related to the development of insulin resistance, diabetes, obesity, dyslipidemia, or hypertension (Lee D H et al., Diabetes Care, 2006, 29(7):1638-44; Lee D H et al., Diabetes Care, 2007, March; 30(3):622-8; Lee D H et al., Diabetologia, 2007 September; 50(9):1841-51) among many other illnesses.

Dioxin compounds, one of the most representative POPs, are called environmental hormone or endocrine disrupter, which have been important issues world widely. Particularly, 2,3,7,8-tetrachlorodibenzo-p-dioxin (TCDD) is the most toxic compound among many environmental hormones and among many artificially synthesized compounds, which is chemically very stable and lasts almost forever in the nature. Once the compound is inside of human body, it is accumulated in fat tissues due to its fat solubility. Some of the compound taken in human body is excreted through urine and bile juice, but the compound is not easily decomposed or excreted in general. In the mouse treated with TCDD, ubiquinone (CoQ) in the liver was reduced and ATP synthesis was suppressed (Toxicol. Appl. Pharmacol. 217: 363, 2006). TCDD induced AhR-dependent ROS generation, resulting in the decrease of mitochondria membrane potential ($\Delta\Psi m$) with inhibiting the functions of mitochondria, and hence metabolic syndrome including diabetes was expected to be developed.

Once dioxin is introduced in a cell, it is specifically linked to arylhydrocarbon receptor (AhR) in cytoplasm. This dioxin-receptor complex is then introduced in the nucleus and the complex is bound to ARNT (AhR nuclear translocator) therein. As a result, the complex is converted into the DNA bindable complex. The transformed DNA bindable complex is strongly conjugated to a specific gene and at this time such specific gene is called dioxin responsive element (DRE). When the dioxin complex is linked to DRE, the neighboring response gene P4501A1 is activated to induce the synthesis of cytochrome P4501A1 enzyme. Then, by those synthesized enzymes, dioxin toxicity is expressed.

It is possible to classify the patients having disease induced by POPs and to analyze the correlation of elimination of such compounds and treatment effect by measuring the concentration of TCDD equivalent (TCDDEq) among many POPs existing in human serum. As a method for measuring dioxin, instrumental method has been widely used. The method for analyzing TCDDEq up to date is exemplified by gas chromatography/mass spectrometry (GC/MS) and cell-based assay. GC/MS enables the analysis of concentration of each pollutant including TCDD and the detection thereof. However, for high-throughput assay, high price has to be paid. In addition, a large amount of serum sample (25~200 ml) is required for the analysis as well. In the meantime, cell-based assay, which is exemplified by CALUX (Chemically Activated Luciferase Expression), is a biological quantification method to detect dioxin compounds by using the cell line secreting luciferase in the presence of dioxin constructed by gene manipulation. Once the cells having DRE and luciferase gene are exposed on dioxin, dioxin is bound to intracellular AhR and ARNT, which is then bound to DRE in the nucleus. Then, luciferase expression is induced thereby and accordingly luciferase is synthesized in proportion to the content of exposed dioxin. Therefore, the changes of luciferase activity can be effectively used as a detection index for dioxin. By the said method, dioxin-like compounds can be measured and TCDD equivalency (TEQ) can also be measured. However, with the recent technology, analysis with the said method takes long and asks a large amount of serum for the extraction or purification process using hexane from human serum samples (at least, 1 ml and of serum is necessary, and generally 10~20 ml of sample is required). When the transient transfection cell line is used, inter-assay variation is very big, leaving a question in reliability. As the number of samples increases, handling speed and reliability decrease. In addition, dioxin extraction step is required. For example, a sample is treated with an organic solvent to extract fat, which is passed through the activated acid silica gel column to purify the fat. Then, dioxin is extracted. Because of the above dioxin extraction and purification process, there is a big difference between the assay value of TCDD standard material and the quantification value of serum TEQ (Michael, H. et al, 2000, Toxicol. Sciences, 54: 183~193).

The conventional methods require high priced equipments for the analysis and the complicated pre-treatment step for sample purification, for which a large volume of organic solvents and other toxic reagents such as radio-labeled materials are used and longer analyzing time is taken. Therefore, it is required to develop and adapt a novel biological method realizing test and quantification with simple pre-treatment step within a short period of time with guaranteeing high detection sensitivity for saving time, effort, and costs.

Thus, the present inventors studied to develop a novel high throughput detection method for POPs which has improvement from the conventional detection methods for POPs and is easy and accurate. As a result, unlike the conventional method requiring pre-treatment step for the purification of dioxin from serum, a novel biological detection method which uses total serum for easy but accurate analysis of multiple samples and is characterized by accurate analysis even with a small volume of serum has been established. Recently, mutant genes and inventions using the same have been accepted as targets for patent application world-widely. Therefore, the present inventors have completed this invention by confirming that DRE gene could be effectively used for the detection of dioxin compounds.

SUMMARY

It is an object of the present invention to provide a novel biological detection method for dioxins in serum and a diagnostic use thereof in metabolic syndrome and related conditions.

To achieve the above object, the present invention provides a novel biological detection method for dioxins in serum, which comprises the following steps:

1) preparing a transformed cell line by introducing a recombinant vector comprising a gene construct, in which at least one of dioxin-responsive elements (DRE) represented by SEQ. ID. NO: 1, a promoter, and a reporter gene are operably linked, into a host cell, wherein the host cell expresses ARNT and AhR endogenously;
wherein the promoter is any one selected from the group consisting of MMTV (Mouse Mammary Tumor Virus) promoter, SV40 promoter, and CMV (cytomegalovirus) promoter,
wherein the reporter gene is any one selected from the group consisting of luciferase, alkaline phosphatase, chloramphenicol acetyl transferase, and β-galactosidase, and
wherein the host cell is the mammalian tumor cell line;
2) preparing a sample by heat-inactivating the total serum isolated from a test subject;
3) culturing the transformed cell line prepared in step 1) with the sample obtained in step 2); and
4) detecting the expression of the protein expressed by the reporter gene in the transformed cell line cultured in step 3).

The present disclosure also describes a method for method for diagnosing diabetes or metabolic syndrome or predicting the likelihood thereof, which comprises the following steps:

1) preparing a transformed cell line by introducing a recombinant vector comprising a gene construct, in which at least one of dioxin-responsive elements (DRE) represented by SEQ. ID. NO: 1, a promoter, and a reporter gene are operably linked, into a host cell; wherein the host cell expresses ARNT and AhR endogenously;
wherein the promoter is any one selected from the group consisting of MMTV (Mouse Mammary Tumor Virus) promoter, SV40 promoter, and CMV (cytomegalovirus) promoter,
wherein the reporter gene is any one selected from the group consisting of luciferase, alkaline phosphatase, chloramphenicol acetyl transferase, and β-galactosidase, and
wherein the host cell is the mammalian tumor cell line;
2) preparing a sample by heat-inactivating the serum obtained from a test subject;
3) culturing the transformed cell line prepared in step 1) with the sample obtained in step 2);
4) detecting the expression of the protein expressed by the reporter gene in the transformed cell line cultured in step 3); and
5) determining the subject to have diabetes or metabolic syndrome if the expression of the reporter gene in the transformed cell line cultured compared to that from a control subject.

The present invention also provides a method for monitoring the prognosis of diabetes or metabolic syndrome, which comprises the following steps:

1) preparing a transformed cell line by introducing a recombinant vector comprising a gene construct, in which at least one of dioxin-responsive elements (DRE) represented by SEQ. ID. NO: 1, a promoter, and a reporter gene are operably linked, into a host cell;
2) culturing the transformed cell line prepared in step 1) after treating the cell line with the serum of a test subject with diabetes or metabolic syndrome treated;
3) detecting the expression of the protein expressed by the reporter gene in the transformed cell line cultured in step 2); and
4) judging that diabetes or metabolic syndrome of the test subject is alleviated, improved or treated when the expression level of the reporter gene detected in step 3) is lowered, compared with that of the control treated with serum of a test subject with diabetes or metabolic syndrome non-treated.

In addition, the present invention provides a preparation method of a foreign protein with the original form.

Advantageous Effect

As explained hereinbefore, the detection method for environmental hormone of the present invention has an improvement from the conventional one that requires the step of purification of dioxins from the serum before measurement and has an advantage of saving time and effort because of using serum as a whole, which thereby enables the analysis with increased accuracy and easiness even with multiple numbers of samples. This method is advantageous in biological detection of environmental hormone in serum owing to the efficiency in analysis with small amount of samples without pre-treatment with hexane. In addition, this method can be used to research the correlation between specific POPs and patients' disease factors by accurately detecting whether POPs such as dioxins are present in the serum. This method can be further used effectively to predict the occurrence of disease and to determine treatability.

BRIEF DESCRIPTION OF THE DRAWINGS

The application of the preferred embodiments of the present invention is best understood with reference to the accompanying drawings, wherein:

FIG. 1A is a picture of an agarose gel illustrating the cloning of the pCYP1A1-luc vector. FIG. 1B depicts a vector map of the pCYP1A1-luc vector.

DETAILED DESCRIPTION

Figure 1A:
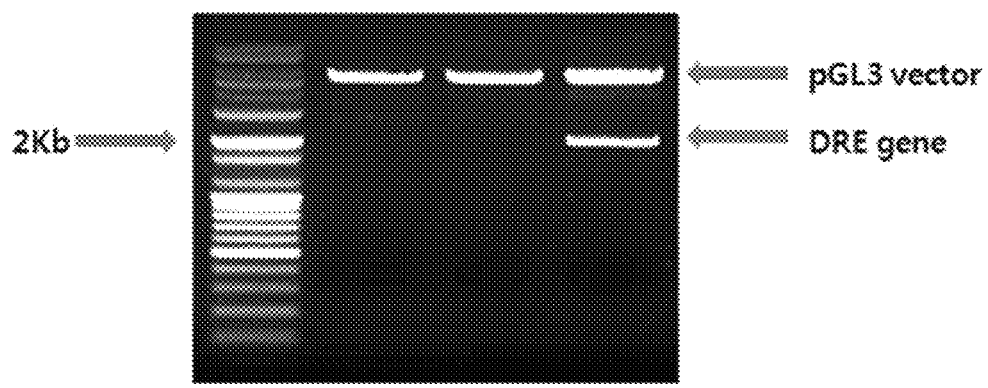
FIGS. 1A-B are a set of diagrams illustrating the cloning of pCYP1A1-luc vector.

Hereinafter, the present invention is described in detail.

The present invention provides a biological detection method for environmental hormone in serum by using a transformed cell line comprising a recombinant reporter gene whose expression is modified by environmental hormone.

Particularly, the said detection method is composed of the following steps, but not always limited thereto:

1) preparing a transformed cell line by introducing a recombinant vector comprising a gene construct, in which at least one of dioxin-responsive elements (DRE) represented by SEQ. ID. NO: 1, a promoter, and a reporter gene are operably linked, into a host cell, wherein the host cell expresses ARNT and AhR endogenously;

wherein the promoter is any one selected from the group consisting of MMTV (Mouse Mammary Tumor Virus) promoter, SV40 promoter, and CMV (cytomegalovirus) promoter, wherein the reporter gene is any one selected from the group consisting of luciferase, alkaline phosphatase, chloramphenicol acetyl transferase, and β-galactosidase, and wherein the host cell is the mammalian tumor cell line;

2) preparing a sample by heat-inactivating the total serum isolated from a test subject;

3) culturing the transformed cell line prepared in step 1) with the sample obtained in step 2); and 4) detecting the expression of the protein expressed by the reporter gene in the transformed cell line cultured in step 3).

The said dioxin compounds are preferably polychlorinated dibenzodioxins (PCDDs), polychlorinated dibenzofurans (PCDFs), polychlorinated biphenyls (PCBs), polycyclic aromatic hydrocarbons (PAHs), flavonoids, or pesticides, but not always limited thereto, and any environmental hormone that can affect transcription activity by combining with the said DRE, in addition to dioxin-like compounds, can be included.

In this method, at least one of the said dioxin-responsive elements of step 1) is included and most preferably 3~4 DREs are included, but not always limited thereto.

In this method, the promoter of step 1) is preferably selected from the group consisting of MMTV (Mouse Mammary Tumor Virus) promoter, SV40 promoter, and CMV (cytomegalovirus) promoter, and is more preferably MMTV (Mouse Mammary Tumor Virus) derived promoter with elimination of glucocorticoid response element region, but not always limited thereto.

Transcription activity of a reporter gene can be determined by the enhancer or cis-acting element near the upstream of a minimum promoter. Therefore, removing enhancer means eliminating other elements that can affect transcription activity.

In this method, the reporter gene of step 1) is preferably selected from the group consisting of luciferase, alkaline phosphatase, chloramphenicol acetyl transferase, and β-galactosidase, and is more preferably luciferase if considering convenience and sensitivity of activity analysis, but not always limited thereto.

The transformed cell line herein indicates the cell line in which the reporter gene is stably expressed. That is, the reporter vector becomes stably a part of a genetic repertory in the host cell once the transformed reporter vector is introduced in the chromosome of the host cell. The stable expression of the introduced gene in the transformed reporter vector can be lasted at least 30 generations.

The host cell of step 1) is preferably eukaryotic, mammalian cell, and more preferably mammalian tumor cell, and most preferably mouse hepatocarcinoma cell line, for example Hepa1c1c7 cell line, but not always limited thereto.

When dioxin is introduced into the cell, it is specifically bound to arylhydrocarbon receptor (AhR), which is introduced into the nucleus. The dioxin-receptor complex introduced in the nucleus is then conjugated to ARNT (AhR nuclear translocator), which is turned into DNA bindable form. Therefore, any cell line that can express ARNT and AhR endogenously can be used as a host cell line.

The transformation herein can be performed by electroporation, plasmogamy, calcium phosphate (CaPO4) precipitation, calcium chloride (CaCl2) precipitation, agitation using silicon carbide fiber, or lipofectamine mediated method, but not always limited thereto.

The conventional detection method for dioxin compounds requires a preprocessing step to extract dioxins through purification of fat extracted from a sample by treating an organic solvent. However, in the method of the present invention, the serum of step 2) is total serum, indicating the serum as a whole can be used.

The serum herein is preferably heat-inactivated for the matter of safety of serum later in the use in the transformed cell line, but not always limited thereto.

In a preferred embodiment of the present invention, mouse CYP1A1 promoter comprising 4 dioxin responsive element (DRE) binding sites (5'-TNGCGTG-3') represented by SEQ. ID. NO: 1 and a recombinant reporter gene vector comprising mouse mammary tumor virus (MMTV) long terminal repeat (LTP) (see FIG. 1) were constructed. Then, Hepa1c1c7, the mouse hepatocarcinoma cell line, was transfected with the same to construct the cell line that can stably express the said recombinant reporter gene (see FIG. 2). With the constructed cell line, 2,3,7,8-tetrachlorodibenzo-p-dioxin (TCDD) response test was performed. As a result, compared with the control not treated with TCDD, luciferase activity was significantly increased when TCDD was treated thereto at the concentration of 10~1000 pM (see FIG. 4). Therefore, the cell line stably expressing the recombinant reporter gene was confirmed to react to TCDD and to activate luciferase effectively.

The present inventors detected dioxins in human serum sample by using the constructed cell line and then analyzed the correlation between dioxin content and physical variables. To prepare serum samples, serums were obtained from 97 people, followed by heat inactivation at 65° C. for 30 minutes for the safety of cell culture. The heat-inactivation herein indicates to eliminate biological activity of serum by heating. Serum contains not only cell growth factors and serum proteins but also complements which are the factors responsible for humoral immunity. Many complements demonstrate cytotoxicity by recognizing cultivated cells, so that when serum is added as a whole to the medium, cell growth is suppressed or worse the cell line might be killed. So, for the safety of cell culture, serum needs to be heat-inactivated.

10 μl of the serum sample prepared above was treated to the cell line stably expressing the recombinant reporter gene, followed by luciferase assay to analyze the correlation between luciferase activity and physical variables. As a result, fold induction values of the serum samples obtained from 97 people were distributed mainly in the range of 2.00~3.00, and the highest rate was detected in approximately 2.50~2.65 fold. The mean fold induction value was approximately 2.35 fold (see FIG. 5).

It was also confirmed by linear regression analysis that there was a significant correlation between dioxin content and many variables factors such as human weight, body mass index (bmi), waist circumference (wc), systolic blood pressure (sbp), diastolic blood pressure (dbp), triglyceride (TG), and fasting blood sugar (fbs). As the values of such factors increased, dioxin fold induction value also increased (see FIG. 6~FIG. 11). Dioxin fold induction value was higher in drinkers/smokers than in non-drinkers/non-smokers. After modifying with all the relevant variables through multivariate analysis, it was confirmed that only drinking or non-drinking was significantly related thereto. It was also confirmed by comparing luciferase levels in serums among impaired glucose regulation (IGR) composed of impaired glucose tolerance (IGT) and impaired fasting glucose (IFG), and diabetes mellitus (DM) and normal glucose tolerance (GNT) that luciferase activity was higher in IGR or DM serum than in NGT serum. In the meantime, there was no significant difference between IGR serum and DM serum. Dioxin fold induction over the number of metabolic syndrome component (MetS component) was also analyzed. As a result, as the number of MetS component increased, dioxin fold induction value increased, and the dioxin fold induction value in MetS patient was significantly increased compared with that in normal people. It was additionally analyzed whether or not the increase of dioxin fold induction was related to the risk of metabolic syndrome or diabetes. As a result, as fold induction value of dioxin increased by 1, the risk of metabolic syndrome and diabetes increased 19.7 times and 11.9 times respectively. Even after the value was modified with bmi, the risk of metabolic syndrome and diabetes was still increased 13 times and 8.7 times respectively as the fold induction value of dioxin was increased by 1. After the value was modified with age, gender, and bmi together, the risk of metabolic syndrome or diabetes was still increased as the fold induction value of dioxin was increased.

Based on the above results, when the method of the present invention was compared with the conventional ones in the aspect of technical matters and effect, it was confirmed as follows: the conventional methods require a preprocessing step to extract dioxins from serum by using an organic solvent like hexane in order to use CALUX analysis system effectively as shown in Table 1. On the other hand, the present invention is advantageous in saving time, costs, and labor by analyzing serum simply heat-inactivated. In the matter of amount of serum necessary for the analysis, the system of the present invention is advantageous. That is, even with approximately 1/1000 of serum required for the analysis by the conventional method, the system of the invention can analyze serum with high efficiency with similar sensitivity to that of the previous method using a large amount of serum.

TABLE 1

| | CALUX analysis system (1) | CALUX analysis system (2) | High-sensitive CALUX analysis system |
|---|---|---|---|
| Reference | Garrison P M et al (1996) Fund. Appl. Toxicol. 30: 194-203 | Han D et al. (2004) BioFactors 20: 11-22 | Present Invention |
| Transformation Vector | Transient pGudLuc1.1 | Stable pGL2-basic | Stable pGL3-basic |
| Pretreatment of serum | Dissolved in DMSO after hexane extraction | Dissolved in DMSO after hexane extraction | Heat-inactivation |
| Serum amount for analysis | 10~20 ml | 1~10 ml | 10 μl |
| Screening system | 24-well system | 96-well system | 96-well system |
| Cell line | Hepa1c1c7 mouse hepatocarcinoma cell line | H1L1.6 mouse hepatocarcinoma cell line | Hepa1c1c7 mouse hepatocarcinoma cell line |
| Sensitivity in human blood | 1 pM~1 nM | 1 pM~1 nM | 1 pM~1 nM |

Therefore it was confirmed that the dioxin content in serum detected by the detection method for dioxins of the present invention was significantly correlated with various physical variables. Unlike the existing methods requiring a preprocessing step for purifying dioxins from a sample, the method of the present invention is advantageous in easy and fast analysis of multiple samples with saving time and labor by using serum as a whole and also advantageous in accurate analysis even with a small amount of each sample. In addition, the transformed cell line harboring a recombinant reporter gene whose expression is regulated by environmental hormone and total serum can be effectively used for the biological detection of environmental hormone in serum with this method.

The present invention also provides a method for predicting the likelihood of diabetes or metabolic syndrome by using a transformed cell line harboring a recombinant reporter gene whose expression is regulated by dioxin compounds.

Particularly, the method for predicting is preferably composed of the following steps, but not always limited thereto:

1) preparing a transformed cell line by introducing a recombinant vector comprising a gene construct, in which at least one of dioxin-responsive elements (DRE) represented by SEQ. ID. NO: 1, a promoter, and a reporter gene are operably linked, into a host cell;

2) culturing the transformed cell line prepared in step 1) after treating the cell line with the serum of a test subject;

3) detecting the expression of the protein expressed by the reporter gene in the transformed cell line cultured in step 2); and 4) determining the likelihood of diabetes or metabolic syndrome when the reporter gene expression is detected in step 3).

The present invention also provides a method for monitoring the prognosis of diabetes or metabolic syndrome by using a transformed cell line harboring a recombinant reporter gene whose expression is regulated by dioxin compounds and total serum.

Particularly, the method for monitoring is preferably composed of the following steps, but not always limited thereto:

1) preparing a transformed cell line by introducing a recombinant vector comprising a gene construct, in which at least one of dioxin-responsive elements (DRE) represented by SEQ. ID. NO: 1, a promoter, and a reporter gene are operably linked, into a host cell, wherein the host cell expresses ARNT and AhR endogenously;

wherein the promoter is any one selected from the group consisting of MMTV (Mouse Mammary Tumor Virus) promoter, SV40 promoter, and CMV (cytomegalovirus) promoter, wherein the reporter gene is any one selected from the group consisting of luciferase, alkaline phosphatase, chloramphenicol acetyl transferase, and β-galactosidase, and wherein the host cell is the mammalian tumor cell line;

2) preparing a sample by heat-inactivating the serum obtained from a test subject;

3) culturing the transformed cell line prepared in step 1) with the sample obtained in step 2);

4) detecting the expression of the protein expressed by the reporter gene in the transformed cell line cultured in step 3); and 5) determining the subject to have diabetes or metabolic syndrome if the expression of the reporter gene in the transformed cell line cultured compared to that from a control subject.

In this method, at least one of the said dioxin-responsive elements of step 1) is included and most preferably 3~4 DREs are included, but not always limited thereto.

In this method, the promoter of step 1) is preferably selected from the group consisting of MMTV (Mouse Mammary Tumor Virus) promoter, SV40 promoter, and CMV (cytomegalovirus) promoter, and is more preferably MMTV (Mouse Mammary Tumor Virus) derived promoter, but not always limited thereto.

In this method, the reporter gene of step 1) is preferably selected from the group consisting of luciferase, alkaline phosphatase, chloramphenicol acetyl transferase, and β-galactosidase, and is more preferably luciferase if considering convenience and sensitivity of activity analysis, but not always limited thereto.

The host cell of step 1) is preferably eukaryotic, mammalian cell, and more preferably mammalian tumor cell, and most preferably mouse hepatocarcinoma cell line, for example Hepa1c1c7 cell line, but not always limited thereto. Any cell line that can express ARNT and AhR endogenously can be used as a host cell line herein.

The transformation herein can be performed by electroporation, plasmogamy, calcium phosphate (CaPO4) precipitation, calcium chloride (CaCl2) precipitation, agitation using silicon carbide fiber, or lipofectamine mediated method, but not always limited thereto.

In this method, the serum of step 2) is total serum that can be used as a whole without a preprocessing step for purifying dioxins from the serum.

The serum is preferably heat-inactivated before it is treated to the transformed cell line for the matter of safety of serum, but not always limited thereto.

The present inventors constructed a transformed cell line successfully transfected with a recombinant reporter gene vector comprising a dioxin responsive element (DRE) binding site, a mouse mammary tumor virus (MMTV) derived promoter, and a luciferase gene in the downstream, and analyzed the correlation between dioxin content in human serum and physical variables using the same. As a result, the significant correlation between dioxin content and human weight, bmi, wc, sbp, dbp, tg, or fbs was confirmed, and further the significant correlation between dioxin content and impaired glucose regulation (IGR) consisting impaired glucose tolerance (IGT) and impaired fasting glucose (IFG), diabetes mellitus (DM), and normal glucose tolerance (NGT) was also confirmed. In particular, the serum of IGR or DM patient demonstrated higher luciferase activity than that of the serum of NGT patient. As the number of metabolic syndrome component (MetS component) increased, fold induction value of dioxin increased, and the fold induction value of dioxin in MetS patient was significantly increased compared with that in normal people. So, it was confirmed that the increase of fold induction value of dioxin raised the risk of diabetes or metabolic syndrome.

Therefore, the significant correlation between dioxin content in serum and diabetes or metabolic syndrome was confirmed. Accordingly, it has been confirmed that the detection method for dioxins of the present invention using the transformed cell line comprising a recombinant reporter gene whose expression is regulated by environmental hormone and total serum can be effectively used for the prediction of the likelihood of diabetes or metabolic syndrome and the prediction of the prognosis.

EXAMPLES

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Figure 1B:
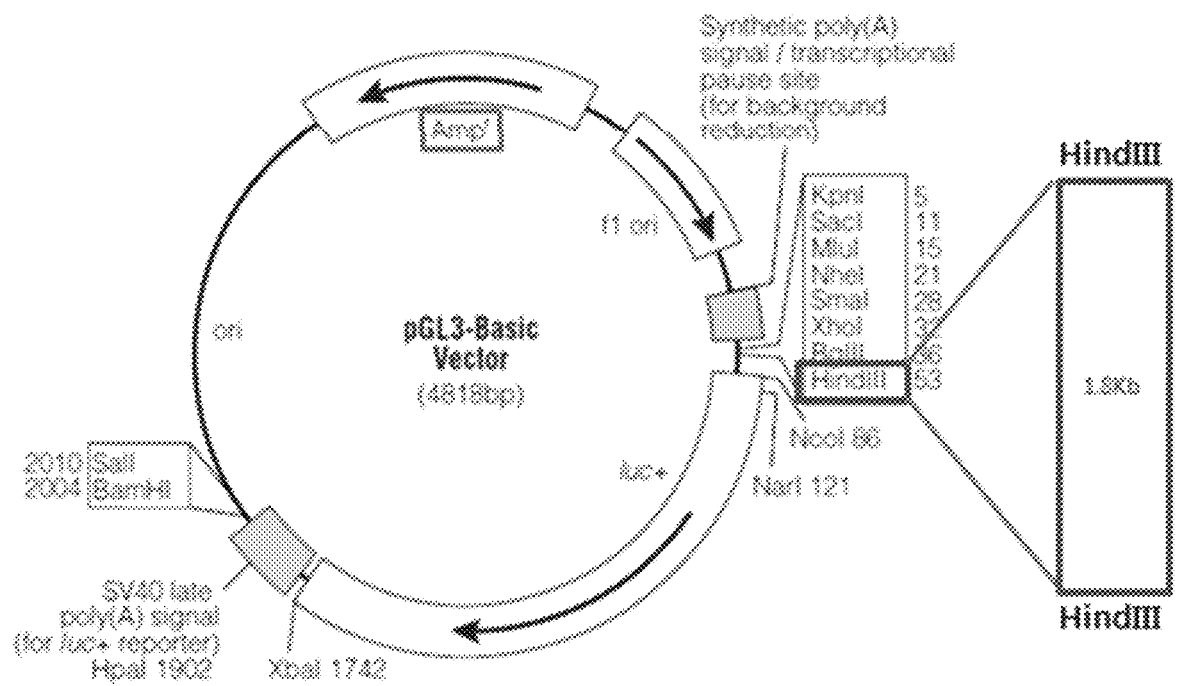

Example 1: Construction of a Cell Line Expressing a Recombinant Reporter Gene Stably <1-1> Construction of a Recombinant Reporter Gene Vector 1.8 kb virus promoter fragment comprising mouse CYP1A1 promoter (482 bp) having 4 DRE binding sites (AhR binding sites) (5'-TNGCGTG-3') and long terminal repeat (LTR) of mouse mammary tumor virus (MMTV) excluding glucocorticoid response element was cut out from pGudLuc1.1 vector by using HindIII, which was cloned in HindIII site of pGL3-basic vector digested with HindIII. As a result, pCYP1A1-luc vector was constructed (Han et al., BioFactors, 20:11-22, 2004). The direction of the promoter was confirmed by sequencing (FIG. 1).

Figure 2:
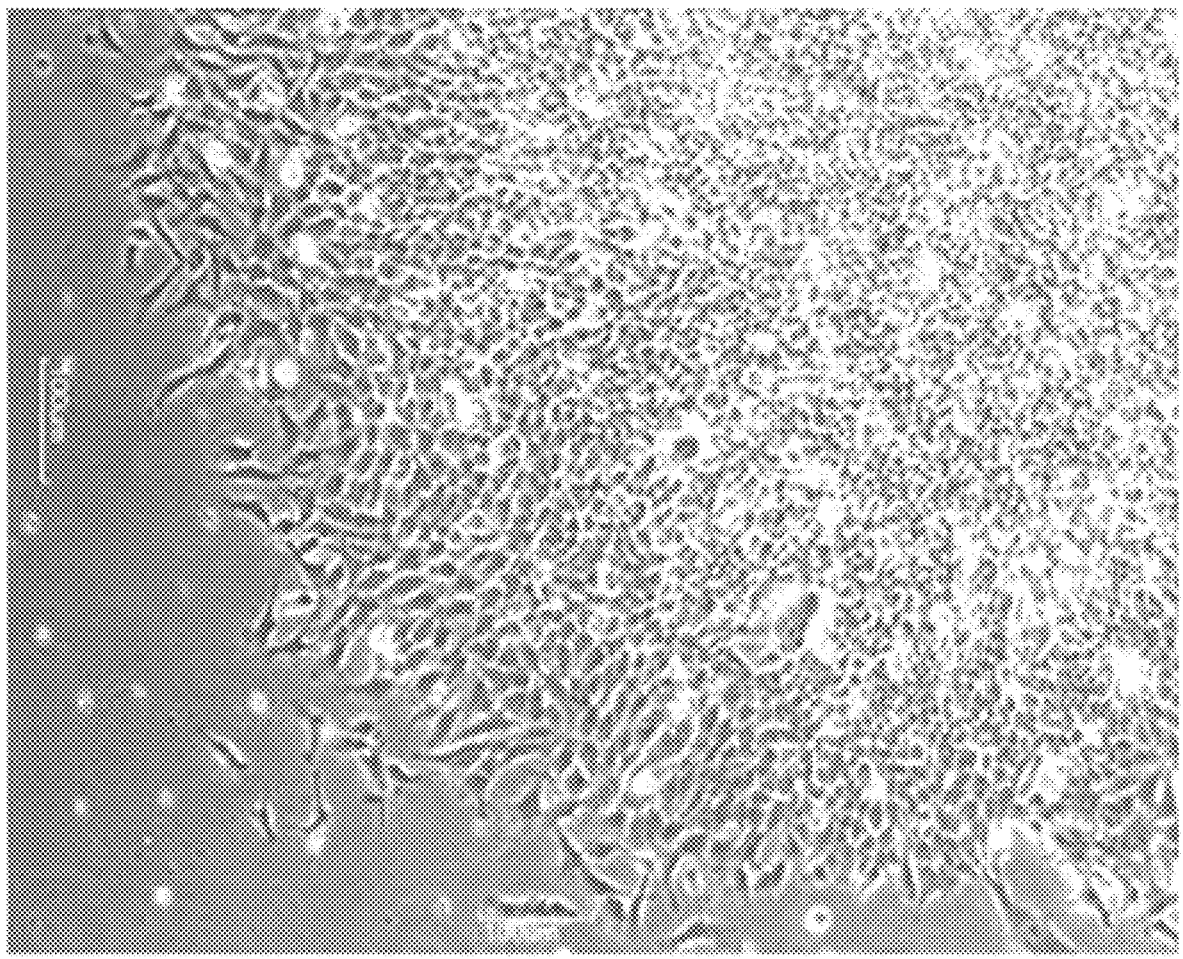
FIG. 2 is a photomicrograph showing the colonies of Hepa1c1c7 cell line expressing pCYP1A1-luc stably.

<1-2> Construction of a Transformed Cell Line Expressing the Recombinant Reporter Gene Hepa1c1c7, the mouse hepatocarcinoma cell line, was distributed in a 6 well plate (1×105 cells/well), followed by culture for 24 hours until the confluency reached 50%. 2 μg of pCYP1A1-luc vector constructed in Example <1-1> and 0.5 μg of pcDNA3.1 vector were added to 100 μl of MEM-α (serum and antibiotic free) and then mixed with 10 μl of Superfect (Qiagen), followed by reaction at room temperature for 10 minutes. Then, 600 μl of MEM-α supplemented with 10% fetal bovine serum (FBS) and 1% penicillin/streptomycin (P/S) was added thereto. 700 μl of Superfect-DNA reaction solution was added to Hepa1c1c7 cells washed with DPBS, followed by culture at 37° C. for 3 hours. Upon completion of the culture, the cells were washed with DPBS and the medium was replaced with 2 ml of fresh MEM-α supplemented with 10% FBS and 1% P/S. 300 μg of G418 was added thereto from 24 hours after the reaction began. G418 resistant cells were collected for 3 weeks. Once colony was formed, each colony was transferred onto 60 mm culture plate (FIG. 2).

Example 2: Response Test with the Transformed Cell Line Expressing the Recombinant Reporter Gene <2-1> Response Test Using Indole-3-Carbinol The cell line stably expressing pCYP1A1-luc constructed in Example <1-2> was distributed in 60 mm culture dish at the density of 1×105 cells, followed by culture for 48 hours. Upon completion of the culture, the medium was replaced with DMEM supplemented with 0.5% charcoal-stripped FBS but not supplemented with phenol red, and indole-3-carbinol was treated thereto at the concentrations of 0, 0.01, 0.1, 1, 10, and 100 μM for 4, 8, or 24 hours. Then, the cells were collected, followed by luciferase assay.

Figure 3:
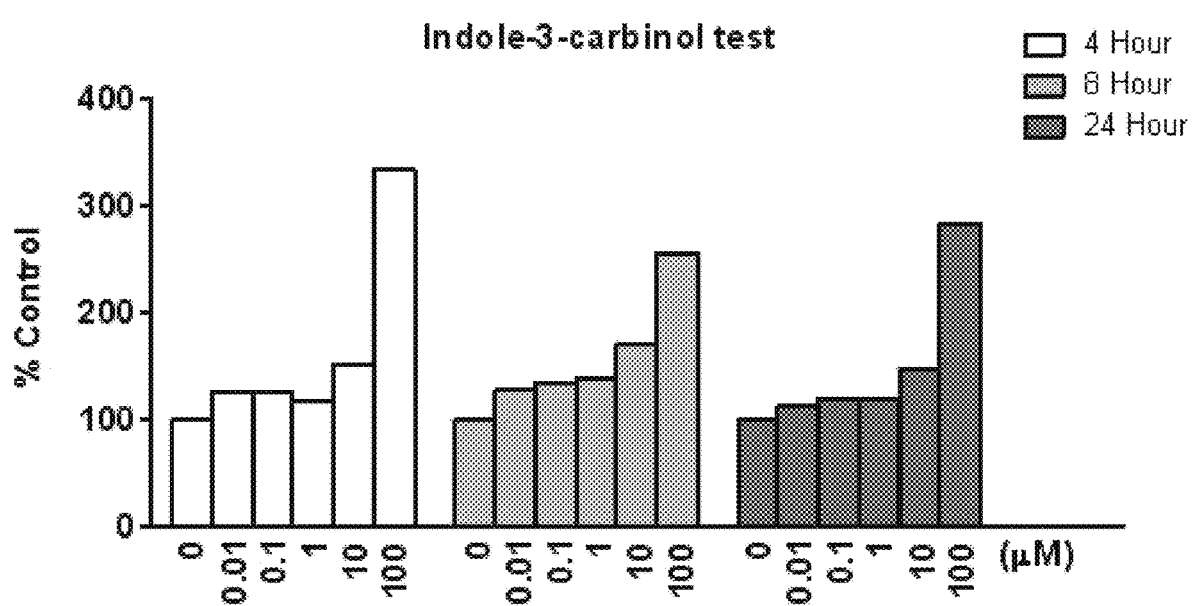
FIG. 3 is a graph illustrating the results of indole-3-carbinol response test with HePa1c1c7 cell line expressing pCYP1A1-luc stably.

As a result, as shown in FIG. 3, luciferase activity of the group treated with 0.001~10 μM of indol-3-carbinol was increased dose-dependently, compared with that of the non-treated control group. In particular, when indol-3-carbionol was treated at the concentration of 100 μM, luciferase activity was increased at least 3 times. At this time, significant difference over the time was not detected (FIG. 3).

<2-2> Response Test Using 2,3,7,8-Tetrachlorodibenzo-p-Dioxin, TCDD)

The cell line stably expressing pCYP1A1-luc constructed in Example <1-2> was distributed in 60 mm culture dish at the density of 2×105 cells, followed by culture for 24 hours. Upon completion of the culture, the medium was replaced with DMEM supplemented with 0.5% charcoal-stipped FBS but not supplemented with phenol red, and 2,3,7,8-tetrachlorodibenzo-p-dioxin (TCDD) was treated thereto at the concentrations of 0, 0.1, 1, 10, 100, and 1000 pM for 4, or 8 hours. Then, the cells were collected, followed by luciferase assay.

Figure 4:
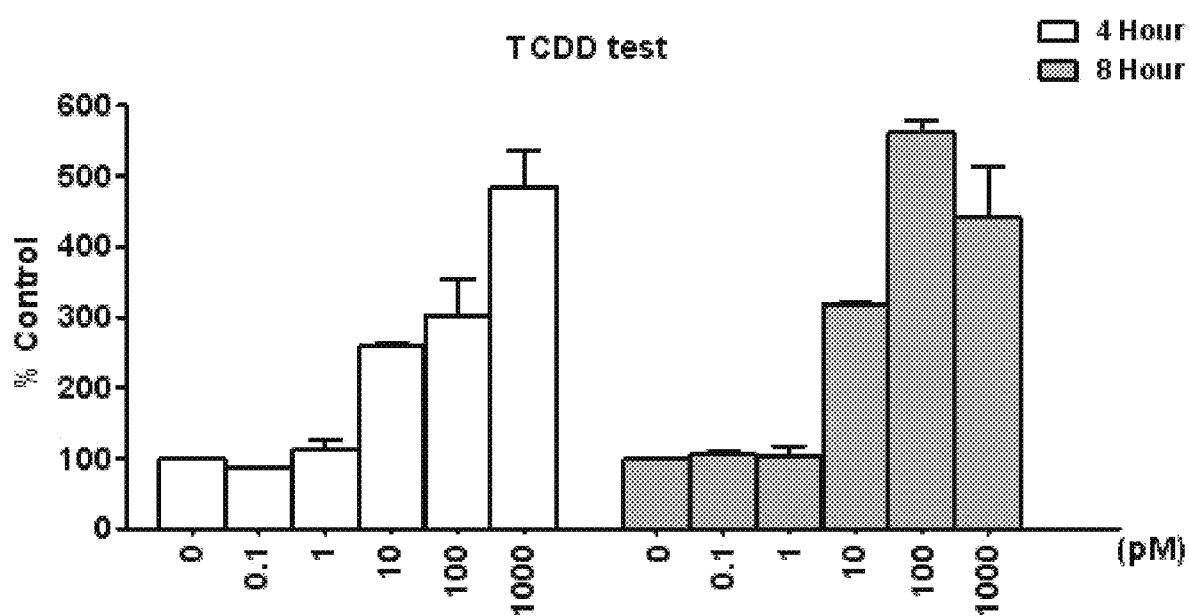
FIG. 4 is a graph illustrating the results of 2,3,7,8-tetrachlorodibenzo-p-dioxin (TCDD) response test with HePa1c1c7 cell line expressing pCYP1A1-luc stably.

As a result, as shown in FIG. 4, the group treated with TCDD at the concentration of 0.1 or 1 pM demonstrated similar luciferase activity to that of the control not treated with TCDD, while the group treated with 10~1000 pM of TCDD demonstrated significantly increased luciferase activity. Luciferase activity was increased over the treatment time, which was not so significant, though (FIG. 4).

Example 3: Detection of Dioxins in Human Serum

<3-1> Preparation of Human Serum Samples

Serum samples obtained from 97 people were heat-inactivated at 65° C. for 30 minutes. This heat-inactivation process secures the safety of cell culture.

<3-2> Detection of Dioxins in Human Serum and Analysis of the Correlation Between Dioxins and Physical Variables The cell line stably expressing pCYP1A1-luc constructed in Example <1-2> was distributed in a 96 well plate at the density of 5×104 cells/well, followed by culture for 24 hours. The medium was replaced with DMEM not containing phenol red (90 μl/well), to which 10% human serum sample was treated (10 μl/well) for 24 hours. Then, the cells of each well were lysed by using luciferase lysis buffer (Promega). The lysate of each well was transferred into a 96 well plate (1 μl/well), followed by protein quantification by BCA method. The remaining cell lysates proceeded to luciferase assay using Promega luciferase assay kit. The luciferase activity was modified with protein concentration and the results were presented by fold induction or % Control.

Figure 5:
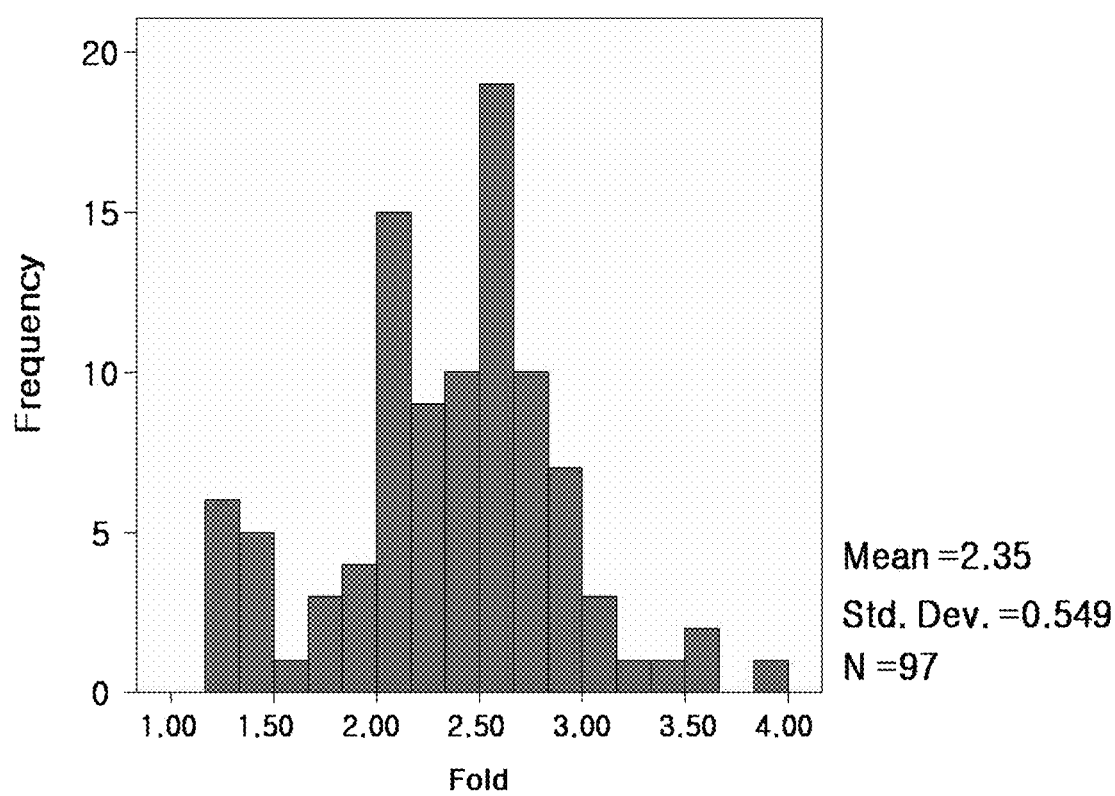
FIG. 5 is a graph illustrating the distribution of dioxin fold induction values.
Figure 6:
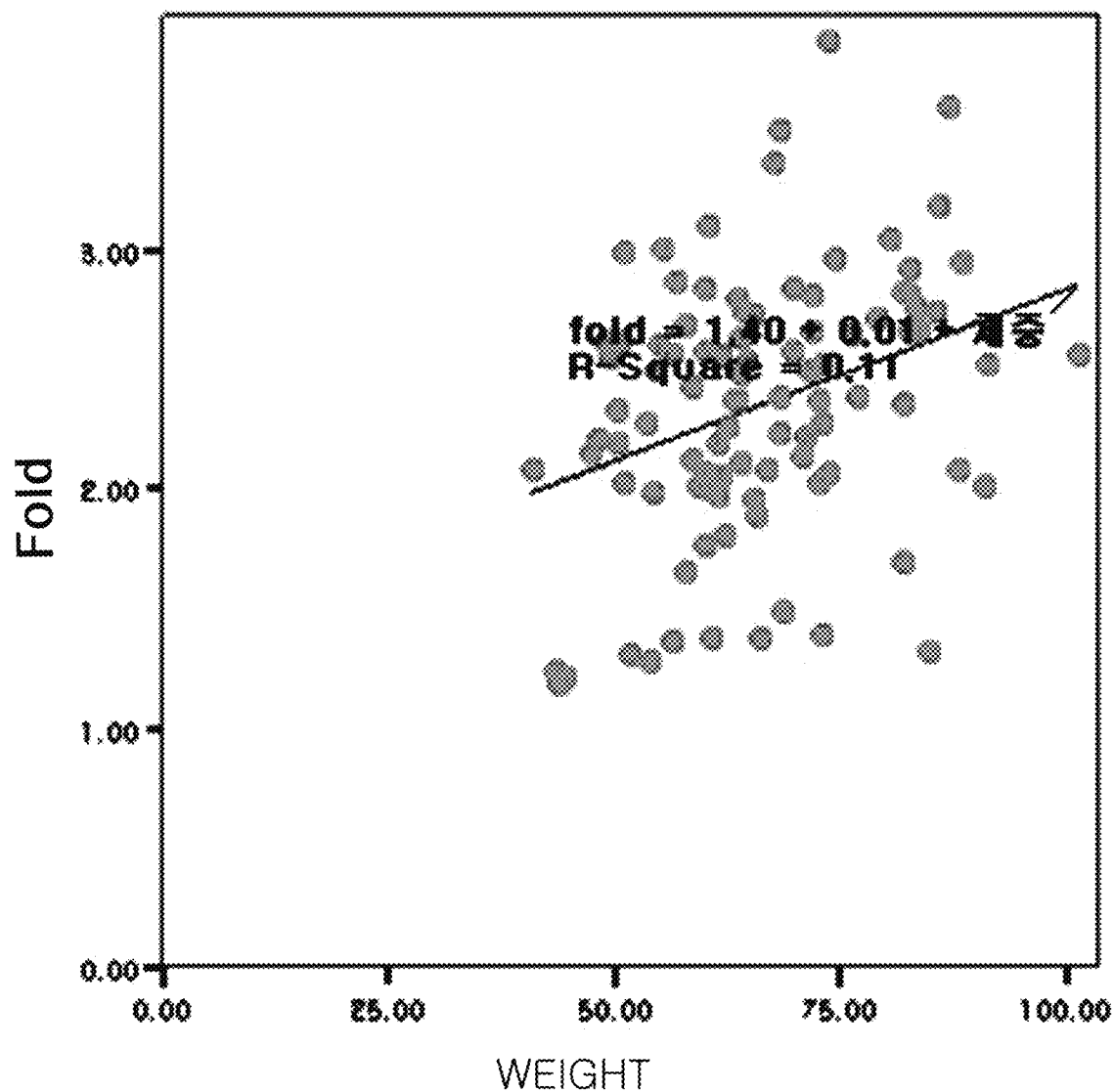
FIG. 6 is a graph illustrating the dioxin fold induction value in human serum over the body weight analyzed by linear regression analysis.
Figure 7:
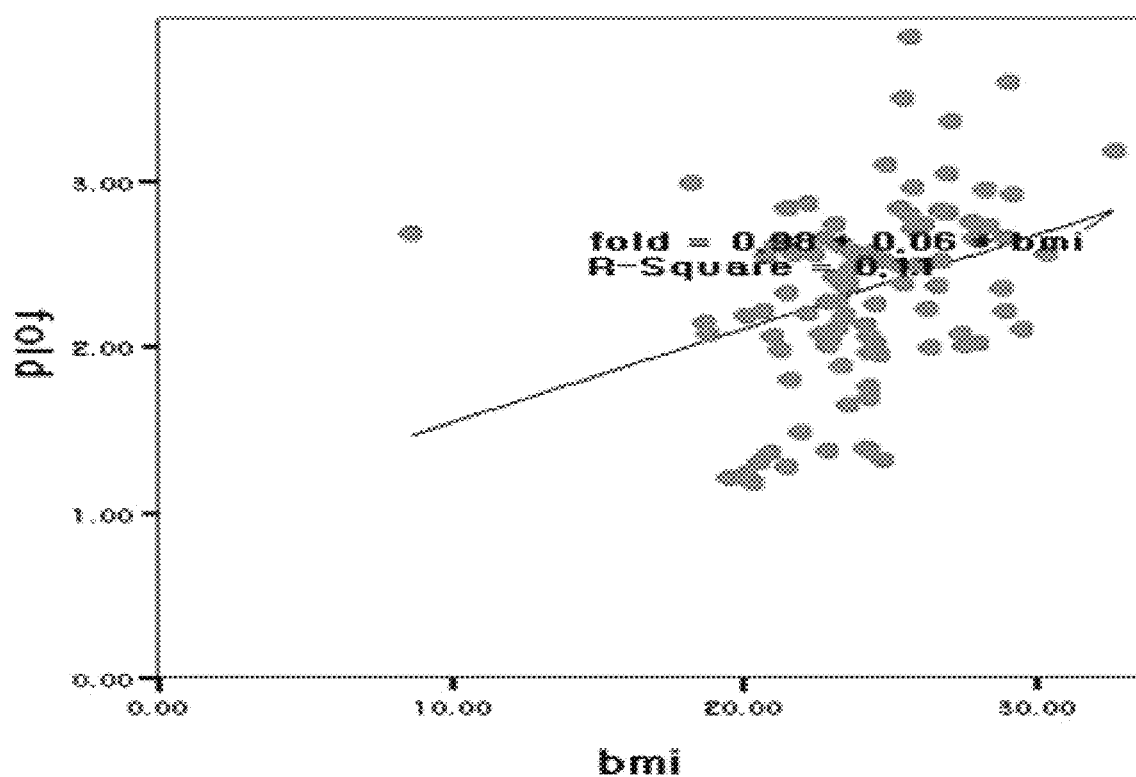
FIG. 7 is a graph illustrating the dioxin fold induction value in human serum over the bmi analyzed by linear regression analysis.
Figure 8:
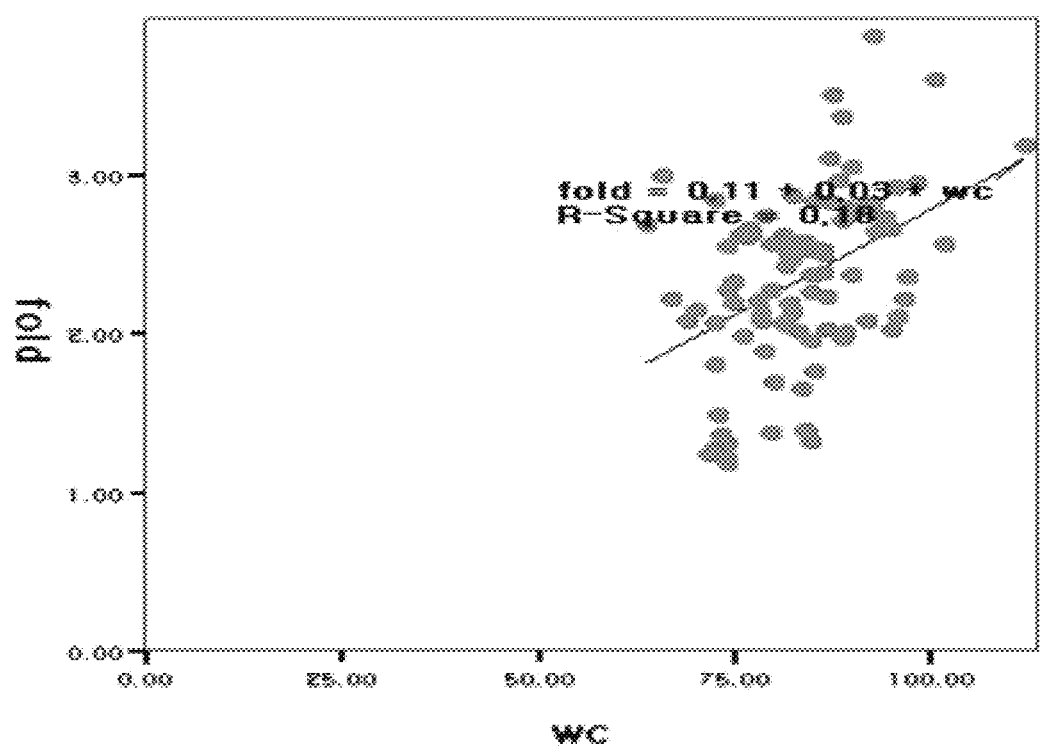
FIG. 8 is a graph illustrating the dioxin fold induction value in human serum over the we analyzed by linear regression analysis.
Figure 9:
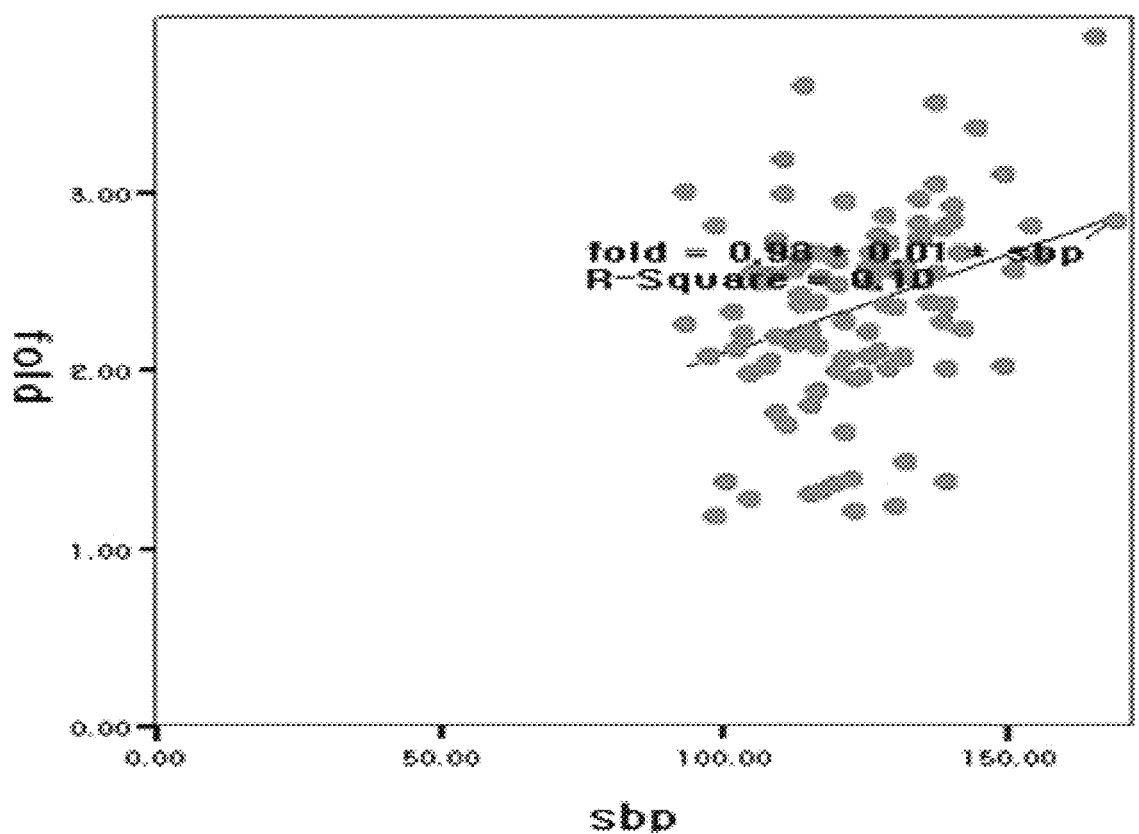
FIG. 9 is a graph illustrating the dioxin fold induction value in human serum over the sbp analyzed by linear regression analysis.
Figure 10:
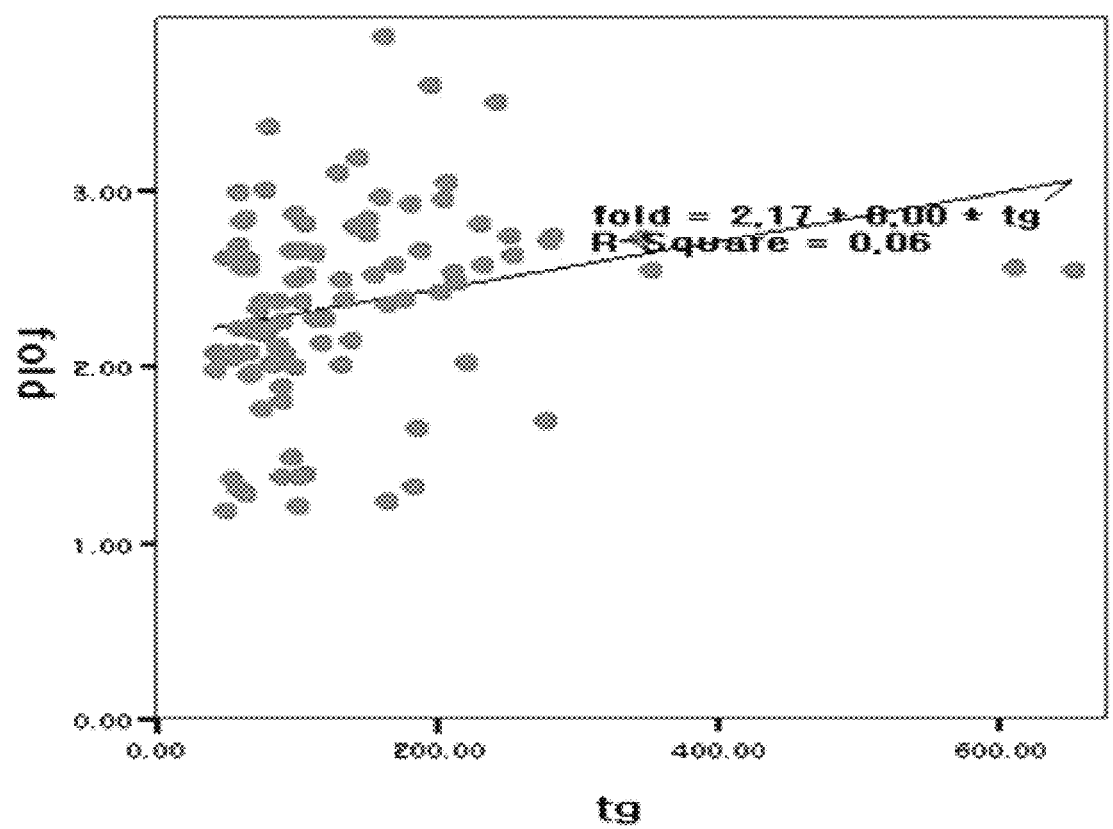
FIG. 10 is a graph illustrating the dioxin fold induction value in human serum over the tg analyzed by linear regression analysis.
Figure 11:
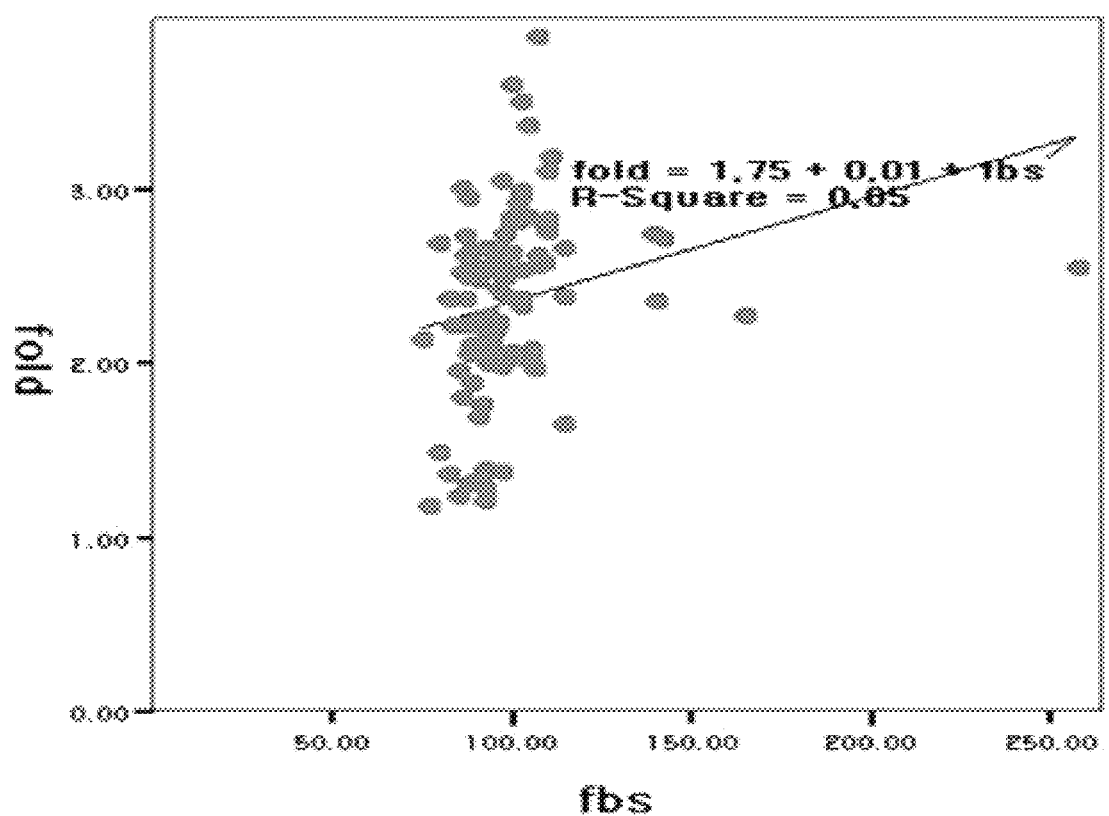
FIG. 11 is a graph illustrating the dioxin fold induction value in human serum over the fbs analyzed by linear regression analysis.

As a result, as shown in FIG. 5, fold induction values of the serum samples obtained from 97 people were distributed mainly in the range of 2.00~3.00 fold, and the highest rate was detected in approximately 2.50~2.65 fold. The mean fold induction value was approximately 2.35 fold (FIG. 5).

The correlation between dioxins and various physical variables was analyzed. As a result, r and P values of each variable are as shown in Table 2. Particularly, as shown in FIG. 6~FIG. 11, it was also confirmed by linear regression analysis that there was a significant correlation between dioxin content and many variables factors such as human weight, body mass index (bmi), waist circumference (wc), systolic blood pressure (sbp), diastolic blood pressure (dbp), triglyceride (TG), and fasting blood sugar (fbs). As the values of such variables increased, fold induction values of dioxin also increased (FIG. 6~FIG. 11).

TABLE 2

|  | r | P value |
| --- | --- | --- |
| Age | 0.0747397 | 0.466872841 |
| Weight | 0.3287115 | 0.001011469 |
| Body mass index (bmi) | 0.3385887 | 0.000740128 |
| Waist circumference (wc) | 0.4194761 | 2.0988E−05 |
| Systolic blood pressure (sbp) | 0.3163346 | 0.001596079 |
| Diastolic blood pressure (dbp) | 0.2696278 | 0.007568065 |
| Serum creatinine (cr) | 0.1057983 | 0.302361753 |
| White blood cell (wbc) | 0.185271 | 0.06924526 |
| got | −0.058096 | 0.571911012 |
| gpt | 0.0216235 | 0.833487555 |
| Cholesterol (chol) | 0.1860382 | 0.068080471 |
| Triglyceride (tg) | 0.2508027 | 0.013218103 |
| High density lipoprotein (hdl) | −0.1656577 | 0.104886065 |
| Low density lipoprotein (ldl) | 0.1170971 | 0.253347357 |
| Fasting blood sugar (fbs) | 0.2320468 | 0.022191056 |
| Hemoglobin A1c (hba1c) | 0.1845205 | 0.070400124 |

Dioxin fold induction value was also investigated in relation to drinking and smoking. As a result, as shown in Table 3 and Table 4, dioxin fold induction value was higher in drinkers/smokers than in non-drinkers/non-smokers.

TABLE 3

|  | Drinking | N | Mean | Std. Deviation | Std. Error Mean |
| --- | --- | --- | --- | --- | --- |
| Fold | No | 43 | 2.1425 | 0.49264 | 0.07513 |
|  | Yes | 50 | 2.5111 | 0.54727 | 0.07740 |

* P = 0.001

TABLE 4

|  | Smoking | N | Mean | Std. Deviation | Std. Error Mean |
| --- | --- | --- | --- | --- | --- |
| Fold | No | 64 | 2.2448 | 0.55652 | 0.06956 |
|  | Yes | 29 | 2.5652 | 0.49577 | 0.09206 |

* P = 0.009

Multivariate analysis was performed by modifying with all the relevant variables. As a result, as shown in Table 5, it was confirmed that only drinking or non-drinking was significantly related thereto.

TABLE 5

| Model | | Unstandardized Coefficients B | Std. Error | Standardized Coefficients Beta | t B | Sig. Std. Error |
|---|---|---|---|---|---|---|
| 1 | Constant | 0.396 | 0.534 | | 0.742 | 0.460 |
| | bmi | 0.031 | 0.017 | 0.188 | 1.878 | 0.064 |
| | sbp | 0.006 | 0.004 | 0.171 | 1.666 | 0.099 |
| | Smoking/Non-smoking | 0.090 | 0.125 | 0.076 | 0.719 | 0.474 |
| | Drinking/Non-drinking | 0.290 | 0.108 | 0.263 | 2.682 | 0.009 |
| | tg | 0.000 | 0.001 | 0.086 | 0.834 | 0.407 |
| | fbs | 0.002 | 0.003 | 0.068 | 0.660 | 0.511 |

Luciferase activity over dioxin was investigated in relation to normal glucose tolerance (NGT), impaired glucose regulation (IGR) composed of impaired glucose tolerance (IGT) and impaired fasting glucose (IFG), and diabetes mellitus (DM). As a result, as shown in Table 6, luciferase activity was higher in the serum of IGR or DM than in the serum of NGT. However, there was no significant difference between the serums of IGR and DM.

TABLE 6

| | NGT N = 50 | | IGR N = 24 | | DM N = 23 | | IGR vs. NGT | DM vs. NGT | DM vs. IGT |
|---|---|---|---|---|---|---|---|---|---|
| | Mean | SD | Mean | SD | Mean | SD | p value | p value | p value |
| Age | 44.1 | 10.3 | 49.0 | 9.3 | 49.3 | 8.5 | 0.052 | 0.037 | 0.894 |
| bmi | 23.2 | 3.5 | 24.7 | 3.1 | 25.6 | 2.4 | 0.084 | 0.004 | 0.246 |
| wc | 80.8 | 7.8 | 85.7 | 9.2 | 87.3 | 7.6 | 0.022 | 0.002 | 0.508 |
| sbp | 116.5 | 11.4 | 130.1 | 16.4 | 129.7 | 16.9 | 0.000 | 0.000 | 0.930 |
| dbp | 68.5 | 8.3 | 76.0 | 9.7 | 77.3 | 11.6 | 0.001 | 0.000 | 0.677 |
| bun | 14.4 | 3.7 | 14.1 | 3.5 | 14.5 | 3.5 | 0.705 | 0.868 | 0.635 |
| cr | 0.8 | 0.2 | 0.8 | 0.2 | 0.9 | 0.1 | 0.771 | 0.111 | 0.140 |
| hb | 14.5 | 1.5 | 14.3 | 1.7 | 14.6 | 1.6 | 0.500 | 0.771 | 0.426 |
| wbc | 6.3 | 1.6 | 6.5 | 1.5 | 6.1 | 1.3 | 0.551 | 0.669 | 0.341 |
| plt | 22.7 | 4.8 | 24.0 | 5.5 | 24.0 | 4.9 | 0.289 | 0.290 | 0.978 |
| got | 23.4 | 6.1 | 23.6 | 7.4 | 25.1 | 7.2 | 0.880 | 0.296 | 0.495 |
| gpt | 23.5 | 8.2 | 23.3 | 13.8 | 27.7 | 17.5 | 0.935 | 0.159 | 0.333 |
| ggt | 27.5 | 17.1 | 40.5 | 39.8 | 56.3 | 43.6 | 0.052 | 0.005 | 0.202 |
| chol | 198.1 | 31.9 | 193.0 | 34.7 | 217.6 | 38.0 | 0.531 | 0.025 | 0.025 |
| tg | 112.2 | 95.2 | 144.9 | 118.5 | 171.9 | 80.1 | 0.206 | 0.011 | 0.367 |
| hdl | 59.8 | 14.2 | 56.0 | 14.9 | 53.6 | 12.7 | 0.299 | 0.081 | 0.558 |
| ldl | 115.9 | 30.3 | 108.0 | 35.1 | 129.6 | 32.4 | 0.322 | 0.083 | 0.034 |
| fbs | 90.0 | 5.6 | 104.5 | 4.3 | 114.5 | 37.1 | 0.000 | 0.005 | 0.211 |
| hba1c | 6.1 | 0.2 | 6.1 | 0.3 | 7.1 | 1.2 | 0.692 | 0.001 | 0.001 |
| Fold (calux) | 2.05 | 0.47 | 2.58 | 0.42 | 2.77 | 0.46 | 0.000 | 0.000 | 0.152 |

Dioxin fold induction was also analyzed over the number of metabolic syndrome component (MetS component). As a result, as shown in Table 7 and Table 8, as the number of MetS component increased, dioxin fold induction value increased. In MetS patients, dioxin fold induction value was significantly increased, compared with that in normal people.

TABLE 7

| MetS component number | Mean | N | Std. Deviation |
|---|---|---|---|
| 0.00 | 2.0191 | 25 | 0.47701 |
| 1.00 | 2.1790 | 23 | 0.44884 |
| 2.00 | 2.4048 | 24 | 0.43824 |
| 3.00 | 2.8263 | 16 | 0.47832 |
| 4.00 | 2.7213 | 6 | 0.71194 |
| 5.00 | 2.6845 | 2 | 0.17577 |
| Total | 2.3461 | 96 | 0.54742 |

* P < 0.001, linear regression analysis

TABLE 8

| | MetS | N | Mean | Std. Deviation | Std. Error Mean |
|---|---|---|---|---|---|
| 배수 | .00 | 72 | 2.1987 | 0.47686 | 0.05620 |
| | 1.00 | 24 | 2.7882 | 0.51367 | 0.10485 |

* P < 0.001, t test

In addition, it was also investigated how the increase of dioxin fold induction was related to the risk of diabetes or metabolic syndrome. As a result, as shown in Table 9~Table 11, every time dioxin fold induction value was increased by 1, the risks of metabolic syndrome and diabetes were increased 19.7 times and 11.9 times respectively. After modifying the result with bmi, every time dioxin fold induction value was increased by 1, the risks of metabolic syndrome and diabetes were still significantly increased 13 times and 8.7 times respectively. After modifying the result with age, gender, and bmi together, the risks of metabolic syndrome and diabetes were still increased.

TABLE 9

|  |  |  | B | S.E. | Wald | df | Sig. | Exp(B) |
|---|---|---|---|---|---|---|---|---|
| Metabolic | Step | fold | 2.981 | 0.776 | 14.742 | 1 | 0.000 | 19.701 |
| syndrome | 1(a) | Constant | −8.565 | 2.033 | 17.750 | 1 | 0.000 | 0.000 |
| Diabetes | Step | fold | 2.478 | 0.686 | 13.066 | 1 | 0.000 | 11.920 |
|  | 1(a) | Constant | −7.374 | 1.802 | 16.742 | 1 | 0.000 | 0.001 |

TABLE 10

|  |  |  | B | S.E. | Wald | df | Sig. | Exp(B) |
|---|---|---|---|---|---|---|---|---|
| Metabolic | Step | fold | 2.577 | 0.808 | 10.160 | 1 | 0.001 | 13.154 |
| syndrome | 1(a) | bmi | 0.260 | 0.109 | 5.701 | 1 | 0.017 | 1.298 |
|  |  | Constant | −14.037 | 3.266 | 18.475 | 1 | 0.000 | 0.000 |
| Diabetes | Step | fold | 2.173 | 0.702 | 9.574 | 1 | 0.002 | 8.788 |
|  | 1(a) | bmi | 0.101 | 0.097 | 1.077 | 1 | 0.299 | 1.106 |
|  |  | Constant | −9.137 | 2.656 | 11.836 | 1 | 0.001 | 0.000 |

TABLE 11

|  |  |  | B | S.E. | Wald | df | Sig. | Exp(B) |
|---|---|---|---|---|---|---|---|---|
| Metabolic | Step | fold | 2.422 | 0.837 | 8.375 | 1 | 0.004 | 11.264 |
| syndrome | 1(a) | bmi | 0.294 | 0.116 | 6.426 | 1 | 0.011 | 1.342 |
|  |  | Age | 0.040 | 0.031 | 1.727 | 1 | 0.189 | 1.041 |
|  |  | Gender | 0.260 | 0.642 | 0.163 | 1 | 0.686 | 1.296 |
|  |  | Constant | −16.789 | 4.135 | 16.488 | 1 | 0.000 | 0.000 |
| Diabetes | Step | fold | 1.961 | 0.707 | 7.701 | 1 | 0.006 | 7.105 |
|  | 1(a) | bmi | 0.103 | 0.102 | 1.026 | 1 | 0.311 | 1.109 |
|  |  | Age | 0.036 | 0.029 | 1.536 | 1 | 0.215 | 1.037 |
|  |  | Gender | −.437 | 0.591 | 0.547 | 1 | 0.459 | 0.646 |
|  |  | Constant | −9.753 | 3.244 | 9.041 | 1 | 0.003 | 0.000 |

INDUSTRIAL APPLICABILITY

As explained hereinbefore, the detection system of the present invention characterized by treating total serum to the transformed cell line harboring the recombinant reporter gene whose expression is regulated by dioxin compounds is advantageous in easy and accurate high efficiency detection of dioxins in serum. Therefore, the detection system of the present invention can be effectively applied to diagnostic techniques for the prediction of disease occurrence and the determination of treatability, based on the consideration of the correlation between dioxin compounds and patient's disease factors.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A detection method for dioxin compounds in serum comprising the following steps:
   1) preparing a transformed cell line by introducing a recombinant vector comprising a gene construct, in which at least one dioxin-responsive element (DRE) of SEQ ID NO: 1, a promoter, and a reporter gene are operably linked, into a host cell, wherein the host cell expresses aryl hydrocarbon receptor (AhR) and AhR nuclear translocator (ARNT) endogenously;

wherein the promoter is any one selected from the group consisting of MMTV (Mouse Mammary Tumor Virus) promoter, SV40 promoter, and CMV (cytomegalovirus) promoter, wherein the reporter gene is any one selected from the group consisting of luciferase, alkaline phosphatase, chloramphenicol acetyl transferase, and β-galactosidase, and wherein the host cell is the mammalian tumor cell line;

2) preparing a sample by heat-inactivating the total serum isolated from a test subject;

3) culturing the transformed cell line prepared in step 1) with the sample obtained in step 2); and 4) detecting the expression of the protein expressed by the reporter gene in the transformed cell line cultured in step 3).

2. The detection method according to claim 1, wherein the dioxin compound is selected from the group consisting of polychlorinated dibenzodioxins (PCDDs), polychlorinated dibenzo-furans (PCDFs), polychlorinated biphenyls (PCBs), polycyclic aromatic hydrocarbons (PAHs), flavonoids, and pesticides.

3. The detection method according to claim 1, wherein the dioxin-responsive element (DRE) of step 1) is included in the gene construct 3 or 4 times.

4. The detection method according to claim 1, wherein the host cell is the mouse hepatocarcinoma cell line.

5. The detection method according to claim 1, wherein the heat-inactivation is performed at 65° C. for 30 minutes.

* * * * *